United States Patent [19]

Desai et al.

[11] 4,159,276

[45] Jun. 26, 1979

[54] METHOD FOR PURIFYING METHYL ALKYL SILOXANE LUBRICANTS

[75] Inventors: Nitin V. Desai, Somerset, N.J.; Richard J. Himics, Trumbull, Conn.

[73] Assignee: RCA Corporation, New York, N.Y.

[21] Appl. No.: 937,837

[22] Filed: Aug. 29, 1978

[51] Int. Cl.$^2$ .............................................. C07F 7/20
[52] U.S. Cl. ............................................. 260/448.2 E
[58] Field of Search ................................. 260/448.2 E

[56] References Cited

U.S. PATENT DOCUMENTS

| | | | |
|---|---|---|---|
| 3,428,530 | 2/1969 | Fauche et al. | 260/448.2 E X |
| 3,440,264 | 4/1969 | McVannel | 260/448.2 E |
| 3,493,595 | 2/1970 | Strasser et al. | 260/448.2 E |
| 3,872,145 | 3/1975 | Breysse et al. | 260/448.2 E |

*Primary Examiner*—Paul F. Shaver
*Attorney, Agent, or Firm*—H. Christoffersen; Birgit E. Morris

[57] ABSTRACT

A method of purifying methyl alkyl siloxane lubricants of the formula

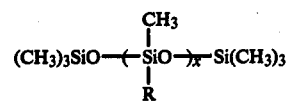

wherein R is an alkyl group of 4–20 carbon atoms and x is an integer which comprises multiply extracting with acetone.

4 Claims, No Drawings

METHOD FOR PURIFYING METHYL ALKYL SILOXANE LUBRICANTS

This invention relates to a method for purifying methyl alkyl siloxane lubricants. More particularly, this invention relates to a method for removing chemically unbound antioxidant from such lubricants.

BACKGROUND OF THE INVENTION

U.S. Pat. No. 3,833,408, herein incorporated by reference, describes the application of methyl alkyl siloxane compositions of the formula

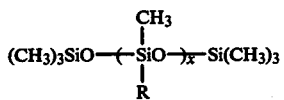

wherein R is an alkyl group of 4–20 carbon atoms and x is an integer, as lubricants for conductive video discs comprising a molded plastic disc having audio and video information in the form of geometric variations in a spiral groove in the surface of the disc. These discs are coated first with a conductive material which acts as a first electrode, then with a dielectric layer and a final layer of lubricant. A metal tipped stylus acts as a second electrode of a capacitor and the information signals are monitored by the stylus which notes changes in capacitance between the stylus and the disc surface as the information, in the form of depressions, passes beneath the stylus.

Further developments in this system have produced a video disc which is made of a conductive plastic material, e.g., a PVC copolymer resin containing sufficient amounts of conductive carbon particles so that the disc can provide capacitance readout, while the plastic resin surrounds the carbon particles providing a dielectric surface layer on the conductive particles. This development has eliminated the need for separate coatings of metal and dielectric on the plastic disc.

Video discs are also being developed which do not require a conductive surface or a grooved surface, the stylus being maintained in synchronization with the information pattern by means of electrical signals rather than the groove walls.

These changes in the materials used for the video disc have somewhat changed the requirements for the lubricant and in certain respects the commercially available methyl alkyl siloxane lubricant, sold by the General Electric Company as SF-1147, wherein R in the above formula is a decyl radical and x is about 2–7, is now unsatisfactory.

This material contains an antioxidant compound which is added as

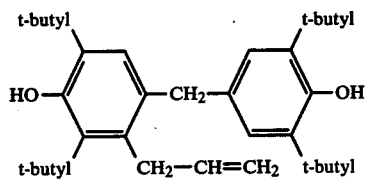

A portion of this antioxidant reacts with residual hydride groups in the methyl alkyl siloxane lubricant, to form chemically bound compounds of the type

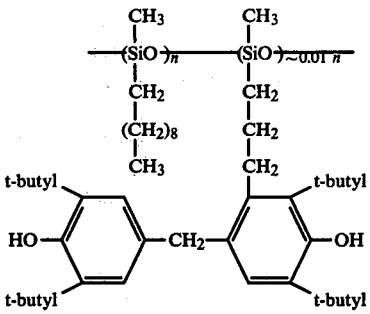

The presence of the unbound, free antioxidant compound can cause changes in the video disc surface with time, contributes to inhomogeneities in the disc surface from one lot to another, particularly in the wetting and lubrication dynamics during playback of the disc, and thus its presence is undesirable. However, in removing the unbound antioxidant, the basic structure of the methyl alkyl siloxane lubricant should remain the same, particularly with respect to molecular weight and molecular weight distribution of the methyl alkyl siloxane molecules. Further, a suitable method for removing antioxidant must not further contaminate the siloxane lubricant with difficult to remove solvents or other material. Further, it is desired that the chemically bound antioxidant also be unaffected to prevent future oxidation or degradation of the lubricant. The present method purifies the methyl alkyl siloxane lubricant, removes chemically unbound antioxidant but without adversely affecting the lubricant or the chemically bound antioxidant so as to improve the performance of this class of lubricants for the video disc application.

SUMMARY OF THE INVENTION

We have found that unbound antioxidant present in commercially available methyl alkyl siloxane lubricants can be selectively removed from the lubricant by a multiple extration with acetone. The resultant lubricant, which is now free of chemically unbound antioxidant but still contains chemically bound antioxidant, is now suitable for use as a video disc lubricant.

DETAILED DESCRIPTION OF THE INVENTION

The present process comprises a multi-step extraction of the methyl alkyl siloxane lubricant with approximately equal volumes of acetone. The siloxane and acetone mixture is stirred together for some period until the antioxidant is dissolved in the acetone. The stirring is controlled so that only one phase is apparent. The mixture is then allowed to stand until two phases are visible, about 4–20 hours, and the siloxane lubricant and acetone phases are separated. The extraction is repeated in like manner until all of the free antioxidant has been removed from the oil layer.

Generally, two extractions are sufficient to remove all the unbound antioxidant completely. A single extraction will remove the bulk of the unbound antioxidant, but minor amounts are still present even when a large excess of acetone is used.

Acetone is the preferred solvent because it is a very effective solvent for the antioxidant, inexpensive, and is readily separable from the siloxane lubricant. After the extraction step, the acetone and siloxane will form distinct layers. If the ambient temperature is low, the lubricant layer can appear hazy due to the presence of small amounts of acetone, but this can be improved by increasing the temperature of the mixture to normal room temperatures.

In order to remove residual acetone from the lubricant layer, the mixture is heated at about 80° C. under vacuum. The bulk of the acetone can be removed at 80° C. using a rotary evaporator with a water aspirator for example and evacuation can be continued at about 80° C. under 10 millimeters of mercury pressure when all the acetone will be removed.

The above procedure produces a methyl alkyl siloxane having the same molecular weight and molecular weight distribution as the feedstock and which contains chemically bound antioxidant but is free of chemically unbound antioxidant. In addition, the process purifies the methyl alkyl siloxane, particularly removing catalyst residues. The losses are low and about 99.5 percent of the starting material is recovered.

The chemically unbound antioxidant-free methyl alkyl siloxane lubricant can be applied to a video disc by evaporation, spin coating or spray coating from solution. For example, a layer about 200-300 angstroms thick of the lubricant can be applied by spray coating from a 1 percent solution of the siloxane in heptane or isopropanol at a loading of from about 0.2 to 2.0 percent by weight of the solution of the methyl alkyl siloxane.

The invention will be further illustrated by the following Example but the invention is not to be limited to the details described therein.

EXAMPLE

2000 Milliliters of a methyl alkyl siloxane lubricant having a viscosity of 46.6 centistokes and a refractive index of 1.4462(23°) and 2000 milliliters of acetone were charged to a vessel fitted with a stirrer, feed lines and stopcock. The mixture was stirred for 4 hours at moderate speed so that only one phase was observed throughout the vessel. The mixture was allowed to stand at room temperature overnight (16 hours). The oil layer was a dark brown/black color. The acetone layer was dark pink, and contained the bulk of the free antioxidant. At the interface, a third layer, black in color, was also collected.

The methyl alkyl siloxane oil layer from the first extraction, about 2050 ml, was charged to the vessel again and an additional 2000 ml of fresh acetone were added. The extraction was carried out as above and 2100 ml of the oil layer were collected. In addition, about 1900 ml of the acetone layer and about 30 ml of a third layer also containing black particles were also collected. The lubricant layer was stripped of acetone on a rotary evaporator at 80° C. under reduced pressure (water aspirator) followed by evacuation at 10 millimeters of mercury pressure and 80° C.

1850 Ml of the methyl alkyl siloxane were recovered. This material had a viscosity of 48.2 centipoises and refractive index of 1.4452 (23°).

No chemically unbound antioxidant was present as determined by gel permeation chromatography and infrared analyses which showed that no olefinic unsaturation was present. These analyses also confirmed the absence of acetone in the lubricant layer.

We claim:

1. A method of purifying a methyl alkyl siloxane of the formula

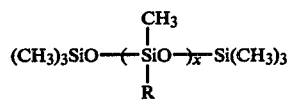

wherein R is an alkyl group of 4-20 carbon atoms and x is an integer containing chemically unbound antioxidant of the formula

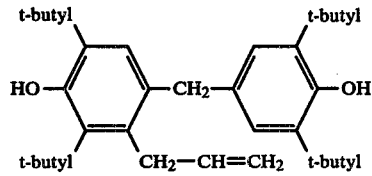

which comprises
extracting the methyl alkyl siloxane with acetone until all of the chemically unbound antioxidant is dissolved in the acetone,
separating the methyl alkyl siloxane and acetone layers and
collecting the chemically unbound antioxidant-free siloxane.

2. A method according to claim 1 wherein the collected layer is treated at about 80° C. under vacuum to remove any acetone present.

3. A method according to claim 1 wherein equal volumes of acetone and methyl alkyl siloxane are employed.

4. A method according to claim 1 wherein two extraction steps and separation steps are employed.

* * * * *